(12) United States Patent
Coszach et al.

(10) Patent No.: US 8,592,609 B2
(45) Date of Patent: Nov. 26, 2013

(54) METHOD FOR OBTAINING LACTIDE

(75) Inventors: Philippe Coszach, Escanaffles (BE); Pierre-Antoine Mariage, Escanaffles (BE)

(73) Assignee: Futerro S.A., Escanaffles (BE)

( * ) Notice: Subject to any disclaimer, the term of this patent is extended or adjusted under 35 U.S.C. 154(b) by 429 days.

(21) Appl. No.: 12/809,216

(22) PCT Filed: Dec. 19, 2008

(86) PCT No.: PCT/EP2008/067994
§ 371 (c)(1),
(2), (4) Date: Nov. 30, 2010

(87) PCT Pub. No.: WO2009/077615
PCT Pub. Date: Jun. 25, 2009

(65) Prior Publication Data
US 2011/0155557 A1 Jun. 30, 2011

(30) Foreign Application Priority Data
Dec. 19, 2007 (EP) .................... 07024679

(51) Int. Cl.
*C07D 319/00* (2006.01)
*C07D 323/04* (2006.01)
*B01D 3/34* (2006.01)

(52) U.S. Cl.
USPC ............... 549/274; 203/33; 203/39; 502/352

(58) Field of Classification Search
USPC ............... 203/2, 3, 33, 39; 549/274; 502/352
See application file for complete search history.

(56) References Cited

U.S. PATENT DOCUMENTS

| 4,504,382 | A | * | 3/1985 | Pine | 208/114 |
| 4,977,122 | A | * | 12/1990 | Eberly | 502/69 |
| 5,236,560 | A | * | 8/1993 | Drysdale et al. | 203/99 |
| 6,048,585 | A | * | 4/2000 | Martyak et al. | 427/99.5 |
| 6,355,772 | B1 | * | 3/2002 | Gruber et al. | 528/354 |
| 8,053,584 | B2 | * | 11/2011 | Meerdink et al. | 549/274 |
| 8,426,615 | B2 | * | 4/2013 | Mariage et al. | 549/274 |
| 2005/0222379 | A1 | * | 10/2005 | Matsuo et al. | 528/359 |

* cited by examiner

*Primary Examiner* — Virginia Manoharan

(57) ABSTRACT

Processes for producing lactide from lactic acid oligomers are described herein. The processes generally include heating a lactic acid oligomer in the presence of a catalyst at a temperature of between 150° C. and 300° C. under a pressure of less than 0.01 MPa to form a lactide; distilling the lactide; and condensing and recovering the lactide, wherein the catalyst is a metal salt of the phosphite anion $PO_3^{3-}$ in which the metal is selected from the group consisting of tin, aluminum, zinc, titanium and zirconium.

9 Claims, No Drawings

METHOD FOR OBTAINING LACTIDE

CROSS-REFERENCE TO RELATED APPLICATIONS

This application claims the benefit of PCT/EP2008/067994, filed Dec. 19, 2008, which claims priority from EP 07024679.8, filed Dec. 19, 2007.

The present invention relates to a process for producing lactide by thermal cracking of lactic acid oligomers.

Lactide or 3,6-dimethyl-1,4-dioxane-2,5-dione is a cyclic dimer of lactic acid. Lactide is an intermediate in numerous industrial processes for the production of polylactic acid, a biodegradable polyester produced from renewable sources. Polylactic acid of high molecular weight has numerous applications in fields such as food packaging and textiles.

One of the routes for the industrial synthesis of lactide consists of a two-stage polymerization/depolymerization process. Lactic acid is first polymerized to give chains having low molecular weights (oligomers) and then these chains are heated in order to depolymerize them to give lactide. The latter is recovered in the vapor phase.

The document GB 2 331 986 A discloses a process for the preparation of a cyclic lactone by heating the oligomer of the corresponding hydroxycarboxylic acid under reduced pressure in the presence of a catalyst and of a phosphorus compound, such as an organic phosphite, a diphosphite or a phosphonite, as stabilizer. This document does not disclose the use of a metal salt of the phosphite anion $PO_3^{3-}$ as catalyst in producing lactide with a low degree of racemization.

Lactide is formed during the production of lactic acid oligomers. The document WO92/05167 discloses that the concentration of lactide in the oligomer is a function of the length of the lactic acid chains produced. This concentration is at a maximum when the mean length of the chains is 2 units. It is reduced as the length of the chains increases. The kinetics of the formation of lactide and its distillation are thus related to the length of the chains of the lactic acid oligomer.

Furthermore, the synthesis of polylactic acid by ring opening has to take place starting from a very pure lactide, one of the essential parameters of which is the low content of free acidity. The document WO 2005/056509 discloses that the molecular weight of the polylactic acid increases as the residual acidity of the lactide acting as starting material for the polymerization decreases.

In order to produce a polymer of high molecular weight (>50 000 daltons), the free acidity has to be less than 20 meq/kg, preferably less than 5 meq/kg.

In point of fact, it is known that the residual acidity of the lactide will decrease as the length of the chains of the lactic acid oligomer from which the lactide is produced by depolymerization increases. In order to do this, it is possible to use chains with mean lengths of greater than 5 lactic acid units, preferably of 10 to 30 lactic acid units, in the presence of an esterification catalyst, in order to increase the kinetics of formation of lactide. The use of catalysts, such as oxides, halogen compounds and organic compounds of metals from Groups 12 (for example Zn), 13 (for example Al) and 14 (for example Sn) of the Table of the Elements, are well known and employed industrially.

Antioxidants can be added to the reaction medium in order to prevent thermal decomposition of the lactic acid and the formation of generally colored by-products. Mention may be made, among these, of Ultranox 626, trialkyl phosphite, aryl/alkyl phosphite mixtures and phenolic compounds.

In the context of the cyclization and distillation of lactide by a thin-film technology, that is to say in a reactor which maximizes the evaporation surface area with respect to the volume of liquid, the catalysts generally described for the production of lactide are tin or zinc dusts, tin or zinc chlorides, or organic salts of tin or of zinc and of organic acids comprising between 1 and 20 carbon atoms. These catalysts are not entirely satisfactory in producing lactide from a lactic acid oligomer.

This is because the divalent tin ($Sn^{2+}$) used in the oxide form increases the kinetics of cyclization only very slightly and is rapidly oxidized to give $Sn^{4+}$, which is much less reactive. When the divalent tin is used in the form of a tin organic compound, such as tin octanoate, the latter rapidly decomposes at high temperature (>200° C.), is oxidized to give $Sn^{4+}$ and loses its reactivity. This decomposition is accompanied by racemization of the lactic acid and by the formation of colored compounds.

Furthermore, the organic part, such as 2-ethylhexanoic acid, can be entrained in the vapor phase and can contaminate the lactide.

With regard to tin halides, such as, for example, $SnCl_2$, their catalytic power is also low and they are rapidly oxidized to give $Sn^{4+}$. Furthermore, the halide anion, such as, for example, $Cl^-$, is highly corrosive and requires specific equipment, such as enameled reactors.

There thus exists a need for a catalyst which increases the kinetics of formation of the lactide starting from lactic acid oligomers which are devoid of the abovementioned disadvantages.

The object of the present invention is to provide a process for producing lactide from lactic acid oligomers in the presence of a catalyst having good reaction kinetics.

Another object of the invention is to provide a process for producing lactide in the presence of a catalyst which is stable to oxidation and to decomposition at high temperature (≥240° C.).

Another object of the invention is to provide a process for producing lactide using a catalyst which does not release volatile compounds, such as, for example, 2-ethylhexanoic acid.

Another object of the invention is to provide a process for producing lactide with a degree of racemization of less than or equal to 4%, preferably of less than or equal to 1%.

Yet another object of the invention is to provide a process which makes it possible to obtain a lactide having the least possible coloring.

Finally, another object of the invention is to provide a process which makes it possible to limit the presence of impurities originating from decomposition reactions.

The present invention provides a process for producing lactide from lactic acid oligomers, the process comprising the following stages:
  (a) heating a lactic acid oligomer in the presence of a catalyst at a temperature of between 150° C. and 300° C. under a pressure of less than 0.01 MPa,
  (b) distilling the lactide resulting from stage (a),
  (c) condensing and recovering the lactide,
  characterized in that the catalyst is a metal salt of the phosphite anion $PO_3^{3-}$ in which the metal is chosen from the group consisting of tin, aluminum, zinc, titanium and zirconium.

The lactic acid oligomer can be an oligomer of general formula HO—[$CHCH_3$—COO]$_n$—H in which n is between 2 and 30. Preferably, n is between 10 and 30.

The lactic acid oligomer is mixed with the catalyst by any appropriate means, for example using a static mixer/exchanger.

Preferably, the catalyst is a metal phosphite in which the metal is chosen from the group consisting of tin and zinc. The term "metal phosphite" is understood to mean the metal salt of the $PO_3^{3-}$ phosphite anion. More preferably, the catalyst is a metal phosphite in which the metal is divalent tin. More preferably still, the divalent tin phosphite is $SnHPO_3$.

The catalyst can be used at a concentration of between 0.1 and 10% by weight, preferably between 0.1 and 5% by weight, more preferably between 0.1 and 3% by weight.

The reaction can be carried out in any type of reactor suitable for the production of lactide. An evaporation reactor is preferred as the lactide can be distilled as soon as it is formed. Examples of reactors of this type are described in Perry's Chemical Engineers' Handbook, 7th edition, chapter 11, pages 107 to 118. Mention may be made, among these, of the forced-circulation evaporator, the short-path evaporator, the tube evaporator, the falling-film evaporator, the thin-film evaporator, the flash evaporator or the disk evaporator.

The reaction is carried out at a temperature of between 150° C. and 300° C., preferably between 230° C. and 280° C., and under a pressure of less than 0.01 MPa (100 mbar), preferably of less than 0.005 MPa (50 mbar), more preferably of less than 0.002 MPa (20 mbar).

The lactide obtained in the reactor is in the vapor form. It can subsequently be optionally distilled at a temperature of greater than 150° C. and a pressure of less than 0.005 MPa (50 mbar) and then condensed to produce a crude lactide comprising lactide, meso-lactide and impurities, such as lactic acid or lactic acid dimers, trimers, tetramers and pentamers.

The crude lactide can subsequently be purified by any technique known to a person skilled in the art, such as by melt crystallization, by distillation or by solvent recrystallization, in order to obtain a lactide sufficiently pure, for example, for the synthesis of polylactide by ring opening.

EXAMPLES

1. Oligomerization of Lactic Acid

The oligomerization of a 90% by weight lactic acid solution was carried out in a stirred glass reactor with a capacity of 5 liters. The water was distilled off at 145° C. and 0.02 MPa (200 mbar). Reflux was set up at 70° C. between the reactor and the condenser such as to recover a portion of the lactic acid entrained in the vapor phase.

After reacting for 8 h, the vacuum was set at 0.008 MPa (80 mbar) and the esterification reaction was continued until a free acidity at 10% and a total acidity of 122% were achieved. The stereospecific purity of the lactic acid oligomer obtained is 98.5%.

2. Cyclization of the Lactide in a Round-Bottomed Flask

The oligomer obtained above was introduced into a round-bottomed flask, then heated to 250° C. and kept stirred. The tin phosphite, $SnHPO_3$, used as catalyst and sold under the name Tib Kat 50 by Goldschmidt, was subsequently introduced into the round-bottomed flask. Various tests were carried out in which the concentration of catalyst was varied (1%, 0.49%, 0.24% and 0.12%). Tin octanoate, frequently used as catalyst for producing lactide from lactic acid oligomer, was used as comparative example.

The round-bottomed flask was surmounted by reflux at 200° C., then by a condenser cooled to 70° C. and finally by a round-bottomed flask for collecting the condensates. The entire assembly was placed under vacuum at between 0.001 and 0.002 MPa (10 and 20 mbar).

The reaction was maintained at 250° C. for 10 minutes. The condensed crude lactide and the oligomer residue were weighed and analyzed, either by gas chromatography after silylation of the carboxyl compounds, in order to determine the contents of the various constituents, or by titration using 0.1M tetrabutylammonium hydroxide of the lactide dissolved in an acetonitrile solution, in order to determine the free acidity and the total acidity. The results of the tests are presented in tables I and II.

The cyclization carried out with tin phosphite makes it possible to obtain a crude lactide with a reduced content of meso-lactide. Compared with tin octanoate, the use of tin phosphite as catalyst thus results in a reduced racemization of the lactic acid oligomer. Given that the starting oligomer has a stereospecificity of 98.5%, the theoretical minimum of meso-lactide observable in the absence of racemization in the crude lactide is 3%. The racemization is calculated by the following formula: [(% of meso-lactide/2)−(100−stereospecific purity of the oligomer, expressed in %)]. Table II discloses that the syntheses carried out using tin phosphite result in degrees of racemization of less than 1%, in contrast to that observed (4.1%) when the synthesis is carried out in the presence of tin octanoate.

The crude lactide does not comprise 2-ethylhexanoic acid when the cyclizations are carried out with tin phosphite.

The coloring of the crude lactide was measured according to the standard ISO 6271-1:2004(F) and is expressed in Hazen units.

The crude lactide produced with tin phosphite is white (coloring of 20 Hazen units), compared with a crude lactide with a yellowish color (coloring of 120 Hazen units) when tin octanoate is used as catalyst.

TABLE I

|  | Starting oligomer weight gr. | Yield (L-lactide/ starting oligomer) % by weight | Residual oligomer | | | Crude lactide formed | |
| --- | --- | --- | --- | --- | --- | --- | --- |
|  |  |  | weight gr. | TA/FA % | L-lactic acid % by weight | weight gr. | L-lactide % by weight |
| (Comparative) Tin octanoate 1% by weight ($Sn^{2+}$: 0.29%) | 200 | 43 | 98.2 | 121.5/4.5 | 84.5 | 101.8 | 85.2 |
| (Example 1 according to the invention) | 207 | 43.3 | 106.6 | 123.1/4.5 | 92.7 | 100.4 | 89.3 |

TABLE I-continued

| | Starting oligomer weight gr. | Yield (L-lactide/ starting oligomer) % by weight | Residual oligomer weight gr. | TA/FA % | L-lactic acid % by weight | Crude lactide formed weight gr. | L-lactide % by weight |
|---|---|---|---|---|---|---|---|
| SnHPO₃ 0.49% by weight (Sn²⁺: 0.29%) (Example 2 according to the invention) | 197 | 37.3 | 115.2 | 123.1/5.1 | 97 | 81.8 | 89.9 |
| SnHPO₃ 0.24% by weight (Sn²⁺: 0.14%) (Example 3 according to the invention) | 204 | 17.9 | 161 | 123.1/5.7 | 97.4 | 43 | 84.9 |
| SnHPO₃ 0.12% by weight (Sn²⁺: 0.07%) | | | | | | | |

FA: free acidity %
TA: total acidity %

TABLE II

| Crude lactide Composition (% by weight) | Tin octanoate (comparative) 1% | SnHPO₃ (invention) 0.49% | SnHPO₃ (invention) 0.24% | SnHPO₃ (invention) 0.12% |
|---|---|---|---|---|
| L-Lactide | 85.2 | 89.3 | 89.9 | 84.9 |
| meso-Lactide | 11.2 | 4.4 | 4.5 | 3.3 |
| Lactic acid | 1.8 | 2.5 | 2.5 | 6 |
| Lactic acid dimer | 0.8 | 1.9 | 1.6 | 3 |
| Lactic acid trimer | 0.2 | 1 | 0.8 | 1.9 |
| Lactic acid tetramer | 0.1 | 0.5 | 0.3 | 0.5 |
| Lactic acid pentamer | 0 | 0.1 | 0.1 | 0.1 |
| 2-Ethylhexanoic acid | 0.6 | 0 | 0 | 0 |
| Lactide + water | 0.1 | 0.3 | 0.3 | 0.3 |
| Racemization % | 4.1 | 0.7 | 0.75 | 0.15 |

3. Stability of the Catalyst Towards Heat

A first cyclization was carried out as described above. Subsequently, during the first recycling of the tin phosphite, the residue from the first cyclization was supplemented with fresh oligomer (newly introduced) and a second cyclization was carried out.

During the second recycling of the tin phosphite, the residue from the second cyclization was supplemented with fresh oligomer and a third cyclization was carried out.

The results are taken up in table III. There is no loss in yield of the cyclization after several successive cyclizations while keeping the same starting catalyst (addition of fresh oligomer to the residue from the preceding cyclization). The tin phosphite thus retains its catalytic activity.

TABLE III

| | Yield (L-lactide/starting oligomer) % | Residual oligomers gr. | Crude lactide gr. | L-Lactide % by weight |
|---|---|---|---|---|
| SnHPO₃ 0.49% by weight | 43.68 | 105 | 101 | 86.5 |
| First recycling of the SnHPO₃ | 42.7 | 106 | 98 | 87.1 |
| Second recycling of the SnHPO₃ | 43.8 | 107 | 98 | 89.4 |

4. Cyclization of the Lactide in a Thin-Film Reactor

The oligomer obtained above (cf. point 1) is mixed with the catalyst and fed at 0.8 kg/h to a stirred glass thin-film reactor with a capacity of 50 cm². The residence time is 10 minutes. The jacket of the reactor is heated to 260° C. and the reactor is placed under vacuum at 0.001 MPa (10 mbar). The vapors of crude produced are recovered by condensation at 80° C.

Table IV shows that the use of tin phosphite as catalyst makes it possible to obtain a greater yield in comparison with that obtained with tin octanoate, for the same concentration of tin: +/−0.88%. The quality of the crude lactide obtained by catalysis with tin phosphite is furthermore much better than that obtained by catalysis with tin octanoate. This is due to the absence of distillation of 2-ethylhexanoic acid and to the absence of racemization.

TABLE IV

| Crude lactide Composition (% by weight) | Tin octanoate (comparative) 3% | SnHPO₃ (invention) 1.5% |
|---|---|---|
| L-Lactide | 89.2 | 93.9 |
| meso-Lactide | 5 | 3 |
| Lactic acid | 1.8 | 1.9 |
| Lactic acid dimer | 0.6 | 0.7 |
| Lactic acid trimer | 0.2 | 0.2 |
| Lactic acid tetramer | 0.1 | 0.1 |
| Lactic acid pentamer | 0 | 0 |
| 2-Ethylhexanoic acid | 3 | 0 |
| Lactide + water | 0.1 | 0.2 |
| Coloring (Hazen units) | 120 | 14 |

TABLE IV-continued

| Crude lactide Composition (% by weight) | Tin octanoate (comparative) 3% | SnHPO$_3$ (invention) 1.5% |
|---|---|---|
| Yield (L-lactide/starting oligomer) | 82% | 87% |
| Racemization % | 1 | 0 |

What is claimed is:

1. A process for producing lactide from lactic acid oligomers comprising:
heating a lactic acid oligomer in the presence of a catalyst at a temperature of between 150° C. and 300° C. under a pressure of less than 0.01 MPa to form a lactide;
distilling the lactide; and
condensing and recovering the lactide, wherein the catalyst is a metal salt of the phosphite anion PO$_3^{3-}$ in which the metal is selected from the group consisting of tin, aluminum, zinc, titanium and zirconium.

2. The process of claim 1, wherein the catalyst is a metal salt of the phosphite anion PO$_3^{3-}$ in which the metal is divalent tin the tin is divalent tin.

3. The process of claim 2, wherein the catalyst is SnHPO$_3$.

4. The process of claim 1, wherein the catalyst is present at a concentration of between 0.1 and 10% by weight.

5. The process of claim 4, wherein the concentration is between 0.1 and 5% by weight.

6. The process of claim 4, wherein the concentration is between 0.1 and 3% by weight.

7. The process of claim 1, wherein the lactic acid oligomer is of formula HO—[CHCH$_3$—COO]$_n$H in which n is between 2 and 30.

8. The process of claim 7, wherein n is between 10 and 30.

9. The process of claim 1, wherein the pressure is less than 0.002 MPa.

* * * * *